United States Patent [19]
Drasler et al.

[11] Patent Number: 5,785,675
[45] Date of Patent: Jul. 28, 1998

[54] THROMBECTOMY DEVICE

[75] Inventors: William J. Drasler, Minnetonka; Robert G. Dutcher, Maple Grove; Mark L. Jenson, Greenfield; Joseph M. Thielen, Buffalo; Emmanuil I. Protonotarios, Brooklyn Park, all of Minn.

[73] Assignee: Possis Medical, Inc., Coon Rapids, Minn.

[21] Appl. No.: 349,664

[22] Filed: Dec. 5, 1994

Related U.S. Application Data

[62] Division of Ser. No. 6,076, Jan. 15, 1993, Pat. No. 5,370,609, which is a continuation of Ser. No. 563,313, Aug. 6, 1990, abandoned.

[51] Int. Cl.$^6$ ............................................. A61B 17/20
[52] U.S. Cl. ............................. 604/22; 604/43; 606/159
[58] Field of Search ..................... 604/22, 27, 30, 604/35, 41, 43–45, 48, 97, 118, 119, 132, 140, 141, 151, 152, 173, 268–269; 128/DIG. 12; 606/159, 167

[56] References Cited

U.S. PATENT DOCUMENTS

| | | | |
|---|---|---|---|
| 4,690,672 | 9/1987 | Veltrup | 604/43 |
| 4,790,813 | 12/1988 | Kensey | 604/22 |
| 4,950,238 | 8/1990 | Sullivan | 604/22 |
| 5,135,482 | 8/1992 | Neracher | 604/22 |

*Primary Examiner*—Corrine M. McDermott
*Attorney, Agent, or Firm*—Hugh D. Jaeger

[57] ABSTRACT

A method of and apparatus for removing a thrombus deposit from the cardiovascular system of a patient without the need to surgically access the location of the thrombus deposit via a cut-down or other surgical procedure. A catheter is inserted percutaneously into the patient at a convenient location either directly or over a previously positioned guide wire. The distal end of the catheter is advanced under fluoroscopy to the site of the thrombus deposit. A balloon is inflated to stabilize the position of the distal end of the catheter within the center of the vessel lumen. A flexible metal tube conveys an extremely high pressure stream of sterile saline solution to at least one jet at the distal end of the catheter. At least one jet positions the thrombus deposit for emulsification by at least one other jet. By directing the jets toward the orifice of the large evacuation lumen of the catheter, a stagnation pressure is induced which propels the emulsion proximally for disposal. The rate of proximal flow of effluent is metered to correspond with the distal flow of saline solution to ensure minimal local impact on the vasculature at the site of the thrombus deposit.

23 Claims, 19 Drawing Sheets

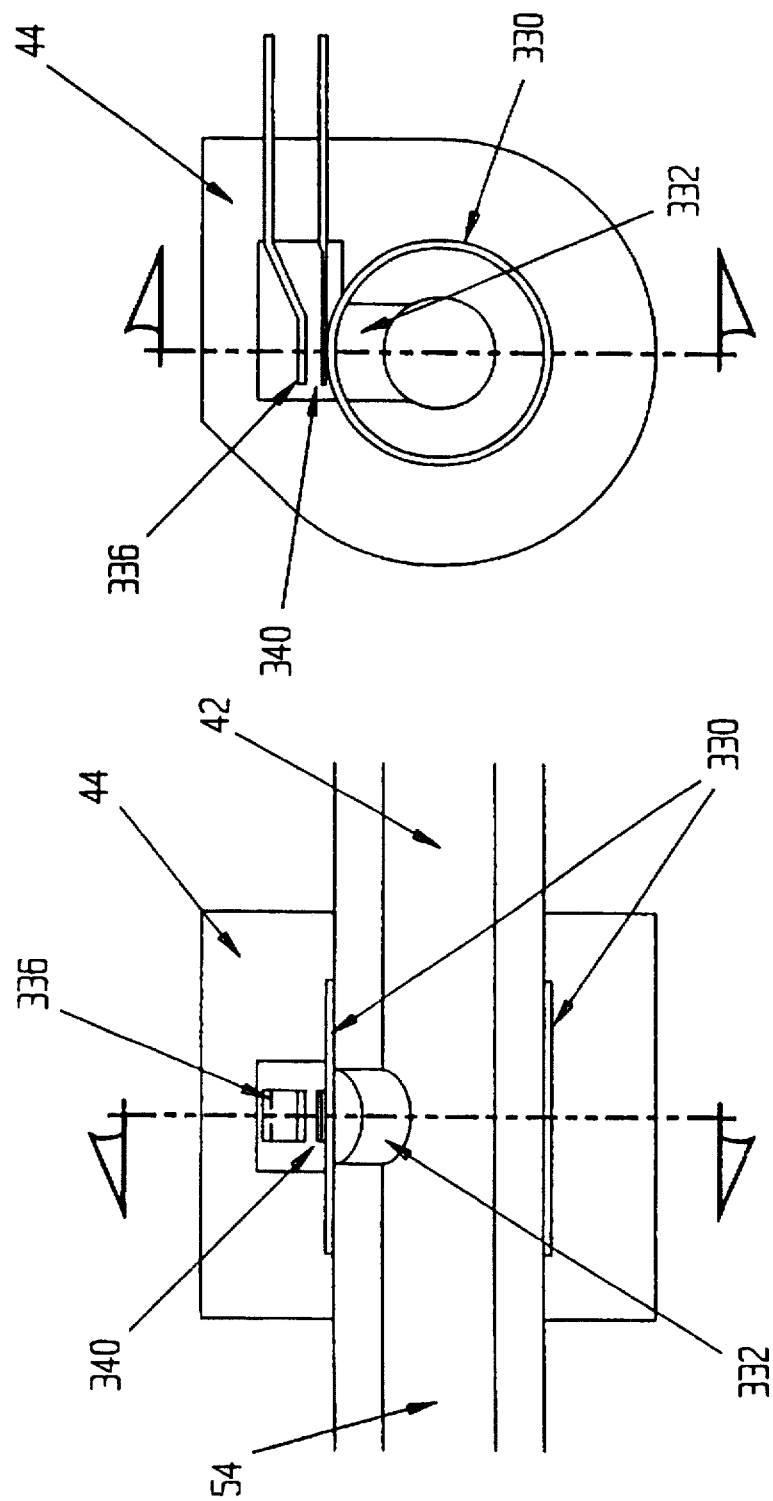

THROMBECTOMY DEVICE

This application is a division, of application Ser. No. 08/006,076 filed Jan. 15, 1993 now U.S. Pat. No. 5,370,609 which is a continuation of Ser. No. 07/563,313 filed Aug. 6, 1990 now abandoned.

BACKGROUND OF THE INVENTION

1. Field of the Invention

The present invention relates generally to medical devices and procedures, and more particularly, relates to medical devices and procedures for removing thrombus deposits from the cardiovascular system.

2. Description of the Prior Art

Procedures and apparatus have been developed for ease in removing tissue and various deposits. U.S. Pat. No. 4,790,813 issued to Kensey and U.S. Pat. No. 4,842,579 issued to Shiber describe techniques for the removal of plaque deposited in arteries by mechanical ablation using rotating cutting surfaces. These relatively traumatic approaches are directed to the treatment and removal of very hard substances.

In current medical procedures, thrombus deposits are often removed using a catheter such as is described in U.S. Pat. No. 4,328,811 issued to Fogarty. In this system, a surgical cutdown is performed to access the vessel and allow catheter entry and advancement to a point beyond the deposit. The balloon is inflated and the catheter is withdrawn pulling the deposit along with it.

Pressurized fluids have also been used in the past to flush undesirable substances from body cavities. U.S. Pat. No. 1,902,418 describes such a system for domesticated animals. The more modern approaches tend to use vacuum rather than gravity as the primary means for removal of the deposits or tissue and relatively low fluid pressures to cut into and fragment the substances to be ablated.

U.S. Pat. No. 3,930,505 issued to Wallach describes a surgical apparatus for the removal of tissue from the eye of a patient. As with similar systems, Wallach uses a relatively low pressure jet of water (i.e. 15 to 3500 psi) to disintegrate the tissue, and a suction pump to perform the actual removal.

A similar approach applied to the cardiovascular system is discussed in U.S. Pat. No. 4,690,672 issued to Veltrup. Veltrup also provides a much lower pressure jet of water (i.e. less than 450 psi) to fragment deposits. As with Wallach, Veltrup uses a vacuum pump for evacuation of the fragments. The distal end of the Veltrup catheter is readily repositionable to permit manual entrapment of the deposits to be fragmented.

SUMMARY OF THE INVENTION

The present invention overcomes the disadvantages of the prior art systems by performing the entire procedure at positive pressures. This eliminates the need for a vacuum pump and provides the added safety feature of an intravascular environment which is always positively pressurized as during normal functioning of the cardiovascular system. This tends to prevent collapse of the vessel. The system also controls the exposure of the vessel to over pressurization and prevent distension.

According to the present invention, the only energy added to the system is via an extremely high pressure stream of saline solution. This stream serves to dislodge thrombus deposits, position them, and then emulsify them. Thrombus particles are attracted to the jet due to the localized high velocity and low pressure. Recirculation patterns and fluid entrainment bring the thrombus continually into close proximity of the jet. Once emulsified by the jet, the particles are removed by flow through the evacuation lumen generated as a result of stagnation pressure which is induced at the mouth of the evacuation lumen by the action of at least one fluid jet directed at and impinging on the lumen mouth.

The procedure is practiced by percutaneously or intraoperatively entering the vascular system of the patient at a convenient location with a cannula. The catheter is inserted either directly or over a previously positioned guide wire and advanced under fluoroscopy to the site of the vascular occlusion or obstruction which generally contains an aggregation of blood factors and cells or thrombus deposit, which is normally identified by angiography. One or more balloons may be inflated to stabilize the distal end of the catheter and provide a degree of isolation of the area to be treated.

Sterile saline is pressurized by a disposable pump and directed through a flexible metallic tube within the catheter. One or more jets at the distal end of the catheter direct the pressurized stream generally in the direction of the mouth of the evacuation lumen at the distal end of the catheter with a component directed toward the vessel wall. One function of the jet(s) alone or in combination with a distal balloon, is to dislodge thrombus deposits from attachment to the vessel wall. Other functions of the jet(s) are to attract and emulsify the thrombus deposits and create the stagnation pressure which evacuates the emulsion.

A metering device is utilized at the proximal end of the evacuation lumen to regulate the flow rate of the emulsified thrombus out of the catheter. Because the entire system operates at a positive pressure, the output must be metered to prevent excess evacuation. Safety monitors turn the system off if one of the lumens or jets becomes clogged. An optional monitor at the distal end of the catheter can monitor power delivery and degree of blockage. An alternative embodiment of the invention provides an extra lumen for monitoring of temperature and/or pressure at the site of the thrombectomy. The evacuation lumen permits the passage of an angioplasty dilatation catheter or angioscope for intravascular viewing.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 16a is a sectioned view of the effluent safety switch; and, FIG. 16b is a cross-sectional view of the effluent safety switch.

DETAILED DESCRIPTION OF THE PREFERRED EMBODIMENTS

Figure 1:
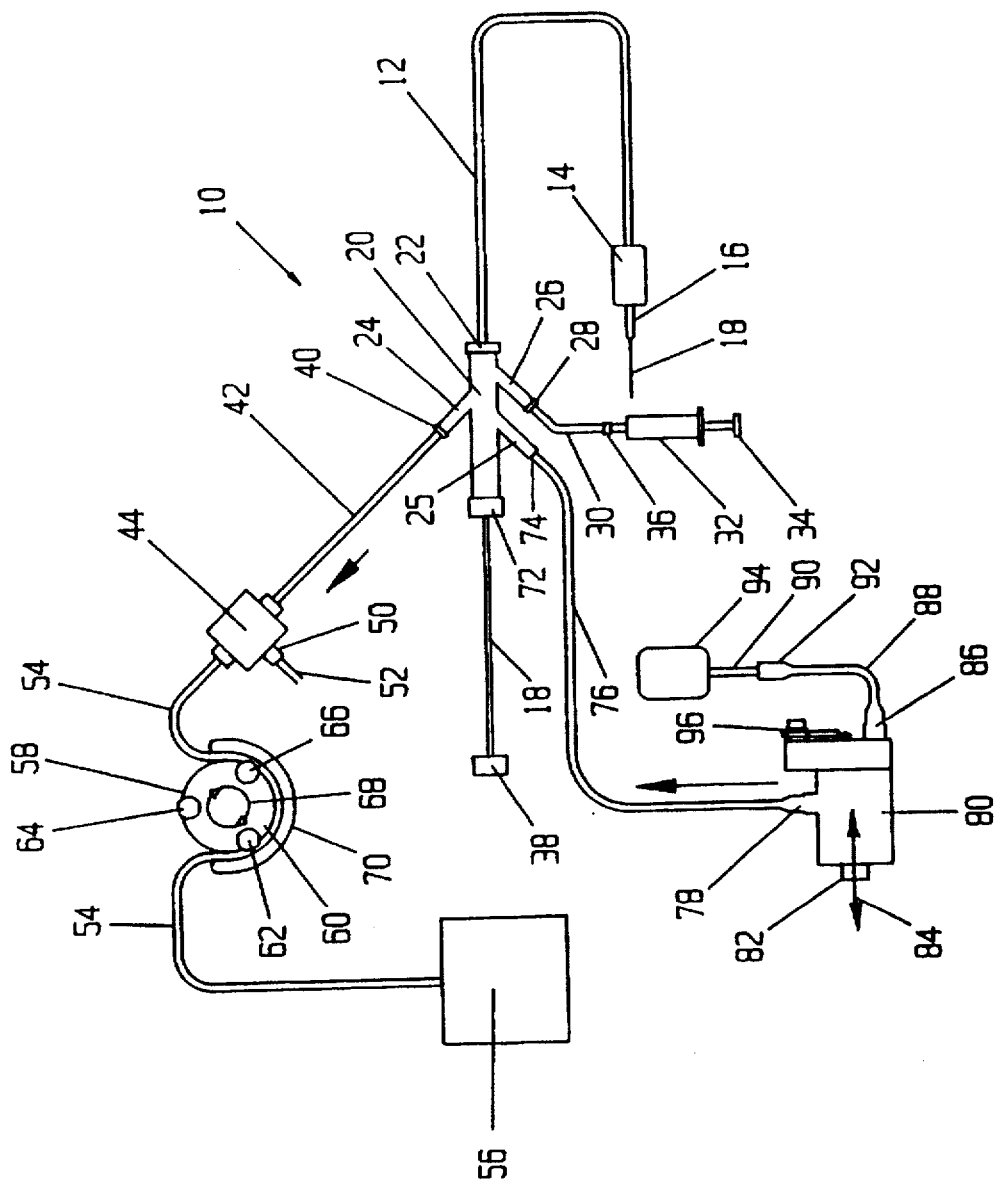
FIG. 1 is a schematic diagram of the overall system employing the present invention.

FIG. 1 is a schematic view of the preferred embodiment of catheter system 10 employing the present invention. The details supplied herein should be taken as representative and not limiting of the many embodiments which may be efficaciously employed within the scope of the present invention.

Catheter system 10 has a standard two lumen catheter 12, which is extruded of a flexible material, such as polyolefin, PTFE, PVC, polyurethane, or other suitable material in the normal fashion. Near the distal end of catheter 12 is located inflatable balloon 14, which is preferably an elastic balloon having no predefined outside diameter size limitation upon inflation. In this manner, balloon 14 can conform to the exact dimensions of the vessel to hold distal end 16 of catheter 12 in a fixed position. Alternatively, inflatable balloon 14 can be an inelastic balloon with a predefined shape and size to permit it to be also used for dilatation as in translumenal angioplasty. Distal end 16 of catheter 12 is described in more detail below.

Guide wire 18, as manipulated by knob 38, is optionally available for positioning catheter 12 as an over-the-wire system. Guide wire 18 passes through the larger of the two lumens of catheter 12 as described in more detail below.

Manifold 20 is molded of a rigid plastic. The main branch couples to the larger of the lumens of catheter 12 and has a standard seal assembly 72 applied to the proximal end to sealingly engage guide wire 18.

Secondary branch 24 is also coupled to the larger lumen to provide for evacuation of the emulsified thrombus deposits. Secondary branch 24 sealingly engages distal end 42 of effluent tubing 54 via seal assembly 40. The operation of safety monitor 44, monitor switch 50, and cable 52 are explained in further detail below.

Flexible effluent tubing 54, including distal end 42, is coupled to safety monitor 44 as described in more detail below. The flow of effluent through flexible effluent tubing 54 is metered by rollers 62, 64, and 66 as rotated by rotor 60 in the direction of arrows 68. It must be emphasized that the effluent in flexible effluent tubing 54 is under pressure and, therefore, need not be pumped by peristaltic pump assembly 58, which merely restricts and meters the flow. This metering could equally well be accomplished with a timed mechanical valve (not shown) which controls the outflow rate. After metering, the effluent from flexible effluent tubing 54 is deposited in disposal bag 56.

Secondary branch 26 of manifold 20 is sealingly coupled to inflation tubing 30 by seal assembly 28. Inflation and deflation of inflatable balloon 14 is controlled by plunger 34 of syringe 32 in the customary manner. Syringe 32 is sealingly coupled to inflation tubing 30 by coupling assembly 36.

The saline solution used to emulsify the thrombus deposit is derived from standard sterile saline bag 94, which may be commercially available. The saline solution is transferred to disposable pump 80 via hypodermic needle 90 and tubing 88 and couplings 92 and 86. This is a low pressure fluid path.

Disposable pump 80 is a positive displacement piston pump. It is made to be completely disposable for sanitary reasons. Disposable pump 80 is driven reciprocally as shown by arrows 84 by a motor driven cam (not shown) against cam bearing surface 82. As a convenient means to correlate infused volume of saline solution with volume of evacuated effluent, a single electric motor can be used to drive both disposable pump 80 and rotor 60. Control of these volumes is important to prevent rupture or collapse of the vessel wall. Closer tolerance control can be achieved at greater complexity using pressure and/or flow meters.

The high pressure output of disposable pump 80 is coupled to tubing 76 by high pressure coupling assembly 78. Tubing 76 has a flexible metallic inner tube inside of a flexible plastic or rubber outer tube as shown in more detail below. Tubing 76 is sealingly coupled to secondary branch 25 of manifold 20 by seal assembly 74. Safety monitor 96 operates as explained below to turn off the drive motor if the tubing or jets become clogged.

Figure 2A:
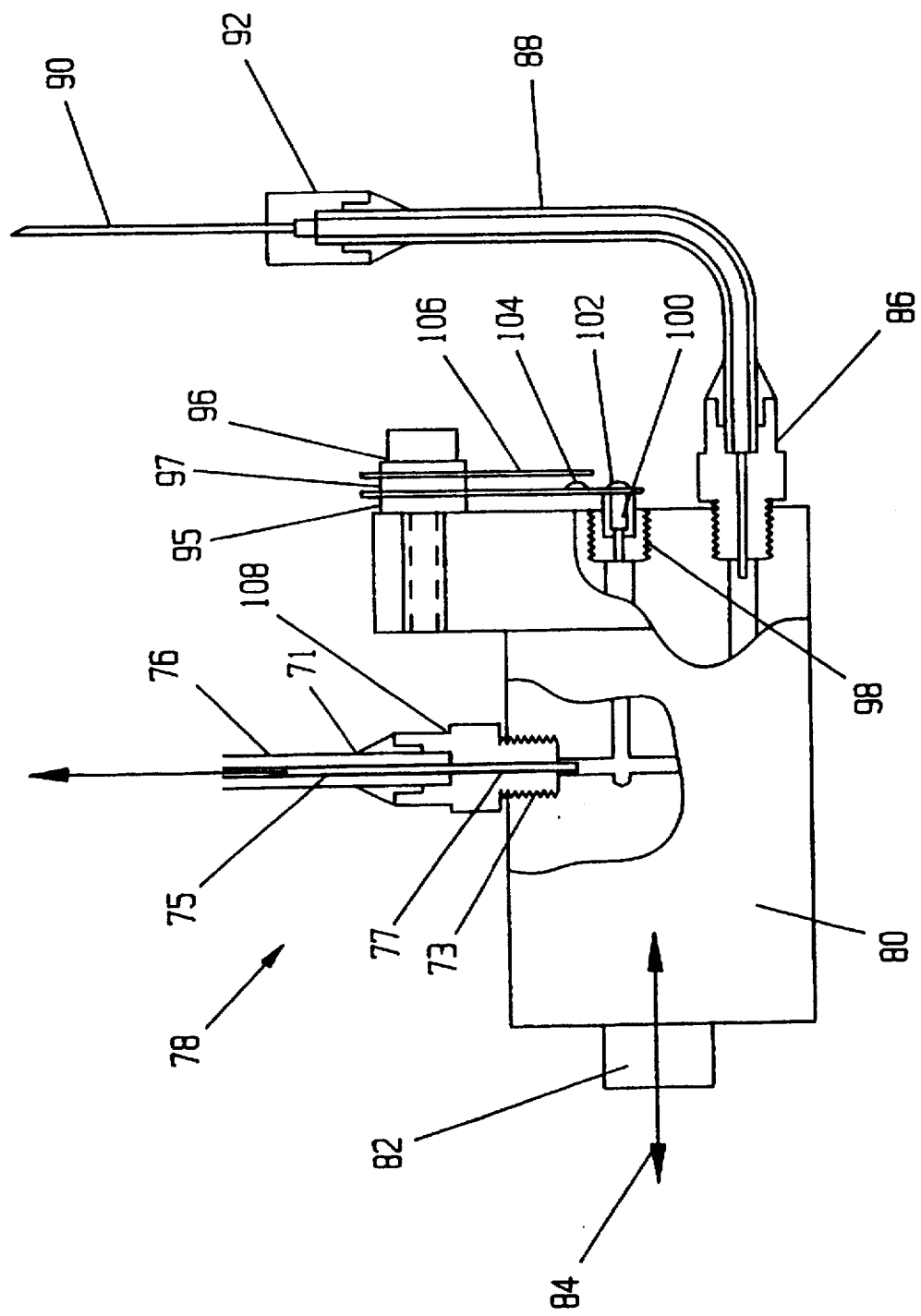
FIG. 2a is a mechanical view of disposable pump.

FIG. 2a is a partially sectioned view of disposable pump 80. As explained above, disposable pump 80 is designed to be discarded after a single use for sanitary reasons. It is a positive displacement piston pump. All referenced components are as previously described.

High pressure coupling assembly 78 is shown in greater detail to highlight that metallic tube 75 is brazed at point 77 to produce the required high pressure joint. Outer tubing 71 is a low pressure connection which may be attached with adhesive. The entire high pressure coupling assembly 78 is attached to disposable pump 80 with threads 73 and compressing a high pressure seal.

Safety monitor 96 comprises two safety features. Pressure plug 100 is attached to disposable pump 80 by threads 98. Pressure plug 100 is designed to release and vent the system to the atmosphere at pressures above 30,000–40,000 psi. The second safety feature serves to electrically disconnect the drive motor whenever the pressure is too high. Increased pump pressure forces contact 104 toward electrical contact with contact 106 as a result of pushing out of pressure plug 100 as attached at point 102 (shown in detail below), thereby closing the electrical circuit to a relay and turning off the drive motor. Insulators 95 and 97 maintain contacts 104 and 106 open under normal pressure conditions.

The saline input to the disposable pump includes a hypodermic needle 90 which penetrates a puncture port on a bag of saline. The saline is delivered through coupling 92 to tube 88 and through coupling 86 into the inlet of the disposable piston pump 80.

Figure 2B:
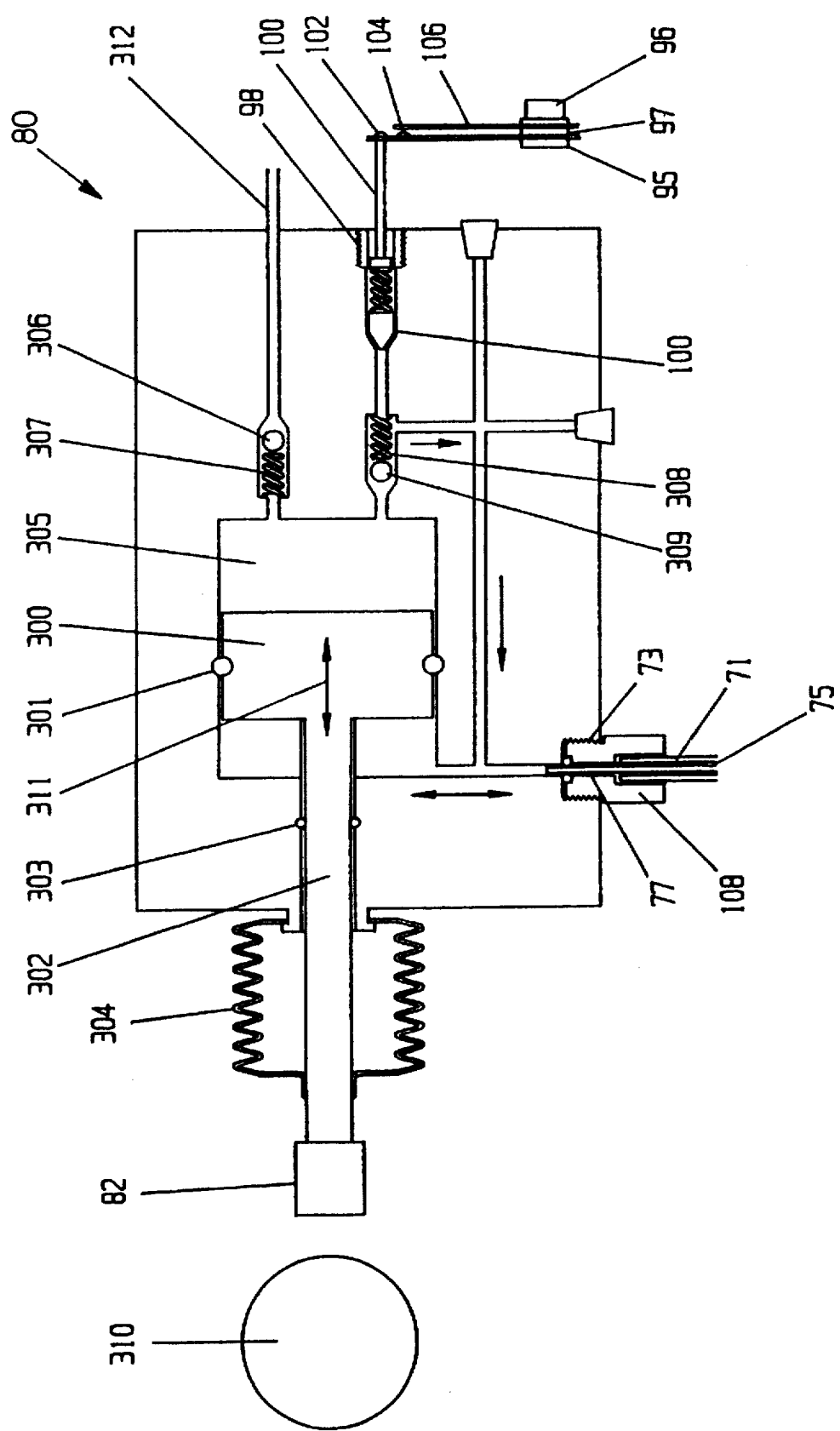
FIG. 2b is a cross-sectional view of the disposable pump.

FIG. 2b is a cross-sectional view of disposable pump 80. As a matter of convenience the disposable pump 80 is oriented slightly different from FIG. 1. All referenced components are as previously-described.

Cam 310 is rotated by a drive motor (not shown) as discussed above. The action of cam 310 imparts a reciprocal motion to cam bearing surface 82 causing connecting rod 302 to move horizontally. This moves piston 300 in the direction of arrows 311. Movement to the left enlarges the effective volume of chamber 305 creating a relatively low pressure. This permits entry of sterile saline fluid from fluid entry port 312 (see also FIG. 1) through ball valve 306 under tension of spring 307.

Movement of piston 300 to the right decreases the effective volume of chamber 305 forcing sterile saline solution to exit via ball valve 309 under sufficient pressure to overcome the tension of spring 308. Note that ball valve 306 will be forced closed as piston 300 is moved to the right. The saline solution is expelled through high pressure tube 75.

Seals 301 and 303 and springs 307 and 308 are selected consistent with the fluid pressures to be developed. Bellows 304 provides an additional seal for the system. Cam 310 may be designed to provide a relatively smooth flow of sterile saline, or it may be implemented as a Geneva or similar cam to enhance the pulsatile delivery of the sterile saline to change the emulsification action at the distal tip of catheter 12.

Pressure plug 100 can be adjusted so that if the pressure reaches an upper limit, such as 30,000—40,000 psi, the pressure will be released and the safety monitor 96 will turn the motor off.

Figure 2C:
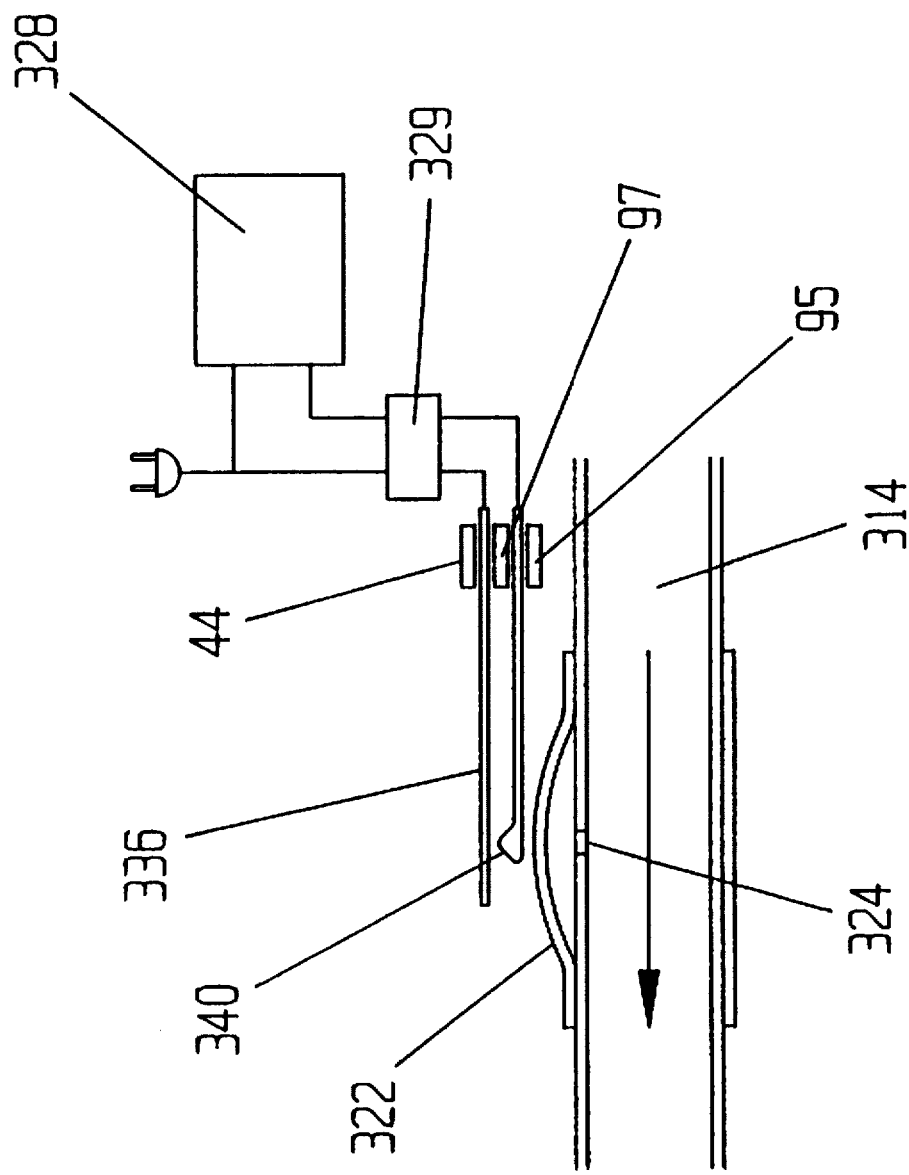
FIG. 2c is a conceptual view of the safety monitor.

FIG. 2c is a schematic view of safety monitor 44. The emulsified thrombus is evacuated in line 314. If the entrance to the evacuation port becomes blocked, the pressure in line 314 will drop and cause membrane 322 to retract around line 314 which has an opening port 324 which has passage to the membrane. As the membrane retracts due to a blockage in the evacuation tube, the contacts 340 and 336 are opened and thereby trigger a relay 329 which will turn off the drive motor 328.

Figure 2D:
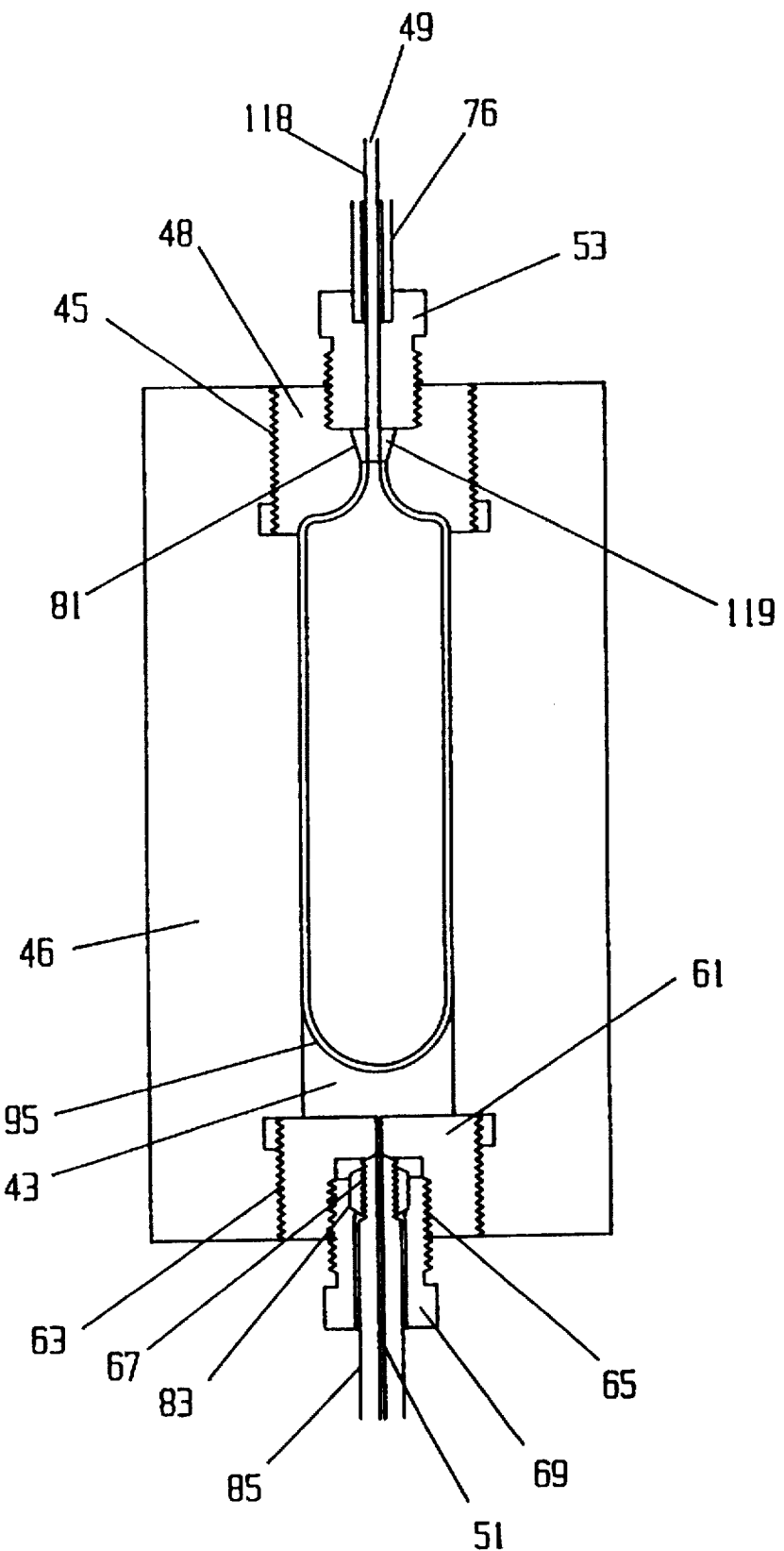
FIG. 2d is a cross-sectional view of an alternative source of pressurized fluid.

FIG. 2d is a cross-sectional view of an alternative source of pressurized fluid. This approach replaces the function of disposal piston pump 80. Using this technique, the high pressure tubing 118, plugs 53 and 48, tapered ring 119, and saline bag 95 are inserted into the conformal housing 46 and tightened down using threads 45. Chamber 43 is pressurized by supplying pressurized non-sterile water or other fluid through inlet 51 forcing sterile saline to exit from port 49 of tubing 118. A seal 81 is made between the bag 95 and the high pressure tubing 76 which delivers the high pressure saline. The high pressure tubing 118 is brazed into a tapered sealing ring 119. A seal is made between the bag 95 and the ring 119 and also between the bag 95 and end plug 48 by tightening down plug 53. The outer plastic tubing 76 is adhesively bonded to plug 53. Bottom plugs 61 and 69 are held in place by threads 63, 65, and 67 and sealed by seal 83 as plug 69 is tightened down.

Whenever employing this alternative embodiment, care must be exercised not to rupture sterile saline bag 95 under the extreme pressures required by the present invention. High pressure fluid is supplied to tubing 85 from a positive displacement pump (not shown).

Figure 3:
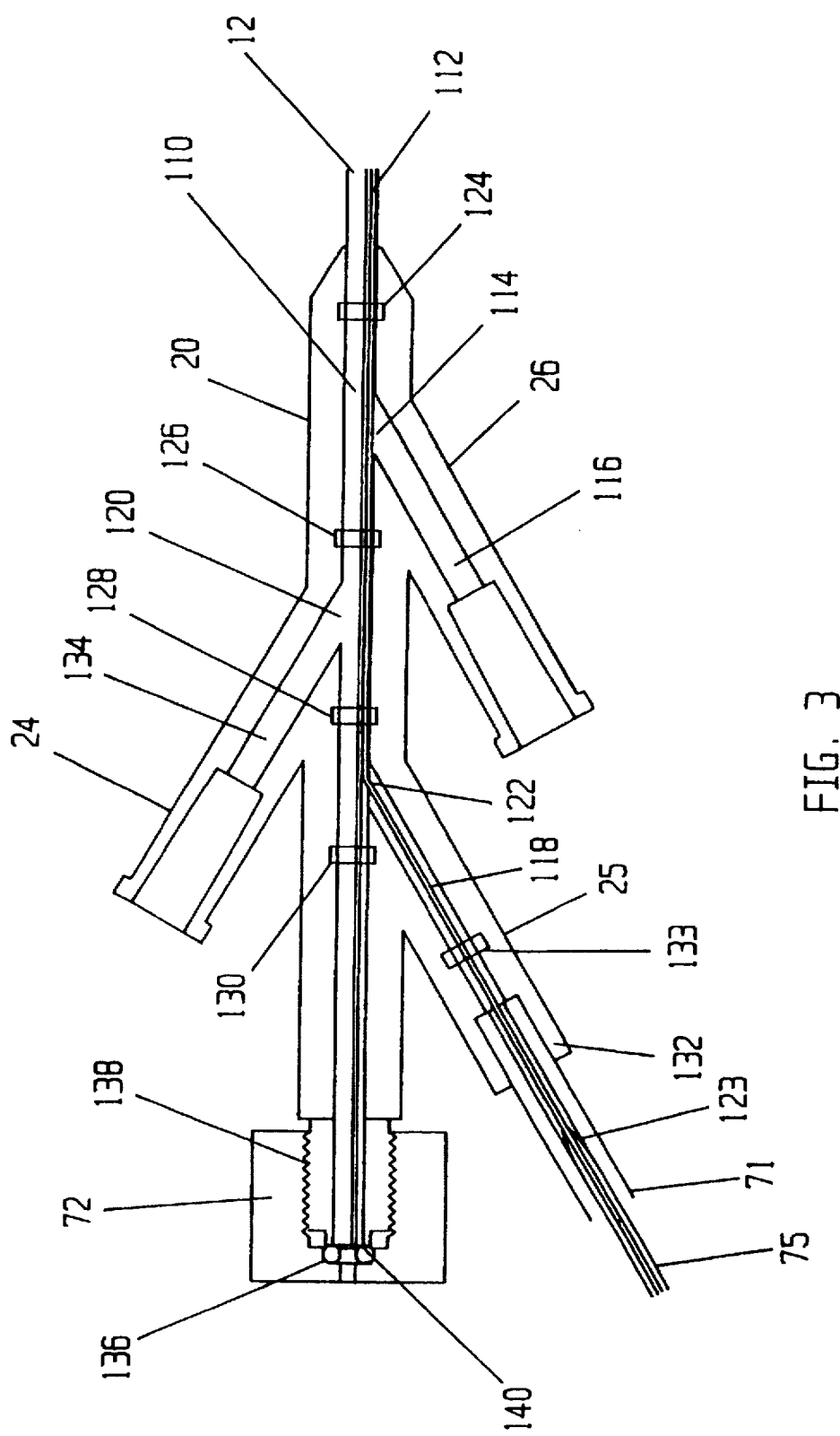
FIG. 3 is a cross-sectional view of the manifold.

FIG. 3 is a cross sectional view of manifold 20. Because this component is molded as two halves, which are solvent-bonded together, the view also happens to show one of the two halves. As explained above, catheter 12 is a two lumen catheter. In the preferred mode, each of the two lumens has two distinct functions. Therefore, manifold 20 serves to provide passage for a high pressure tubing and balloon inflation through one lumen and passage of a guide wire and evacuation through the other lumen.

The larger lumen of catheter 12 is lumen 110. It is used for passage of guide wire 18 (not shown in this view) and for evacuation of effluent and possible passage of an angioplasty dilatation catheter or angioscopic probe. Lumen 110 terminates inside the manifold 20 at the proximal end of the flexible tubular member and provides passage of a guide wire or other diagnostic or therapeutic device. Guide wire 18 is sealed by compressible circular seal 136 which is compressed by surface 140 as threaded knob 72 is tightened on threads 138. It is important to seal guide wire 18 in this way as guide wire 18 must be movable with respect to catheter 12 to properly manipulate distal tip 16 of catheter 12 into position.

Lumen 110 is also terminated at secondary branch 24. This is accomplished by removing a portion of the outer wall of lumen 110 at point 120. This provides fluid coupling between lumen 110 and lumen 134 of secondary branch 24.

The smaller lumen of catheter 12 is lumen 112. One of its functions is as a fluid passageway for the inflation of balloon 14. This function is accomplished by removing a portion of the outer wall of lumen 112 at point 114 to fluid couple lumen 112 to lumen 116 of secondary branch 26.

The remaining purpose of lumen 112 is to provide for passage of metallic tubing 118. Because of the extremely high pressures involved, the saline solution is conveyed in a metallic tubing 118, which is preferably stainless steel hypo tubing. To handle the pressures involved, the hypo tubing is run as a continuous length along catheter 12. The proximal end of metallic tubing 118 passes through the outer wall of lumen 112 and into secondary branch 25. A larger diameter hypo tube is brazed onto hypo tube 118 at point 123. This larger tubing is covered by protective plastic tubing 71. Manifold 20 is solvent-bonded together prior to assembly of the catheter, and points 124, 126, 128, 130 and 133 are used to introduce an adhesive which serves as a seal to separate each path and each lumen. Point 132 shows the bonding of the outer plastic tube which surrounds the high pressure supply tube to the manifold.

Figure 4:
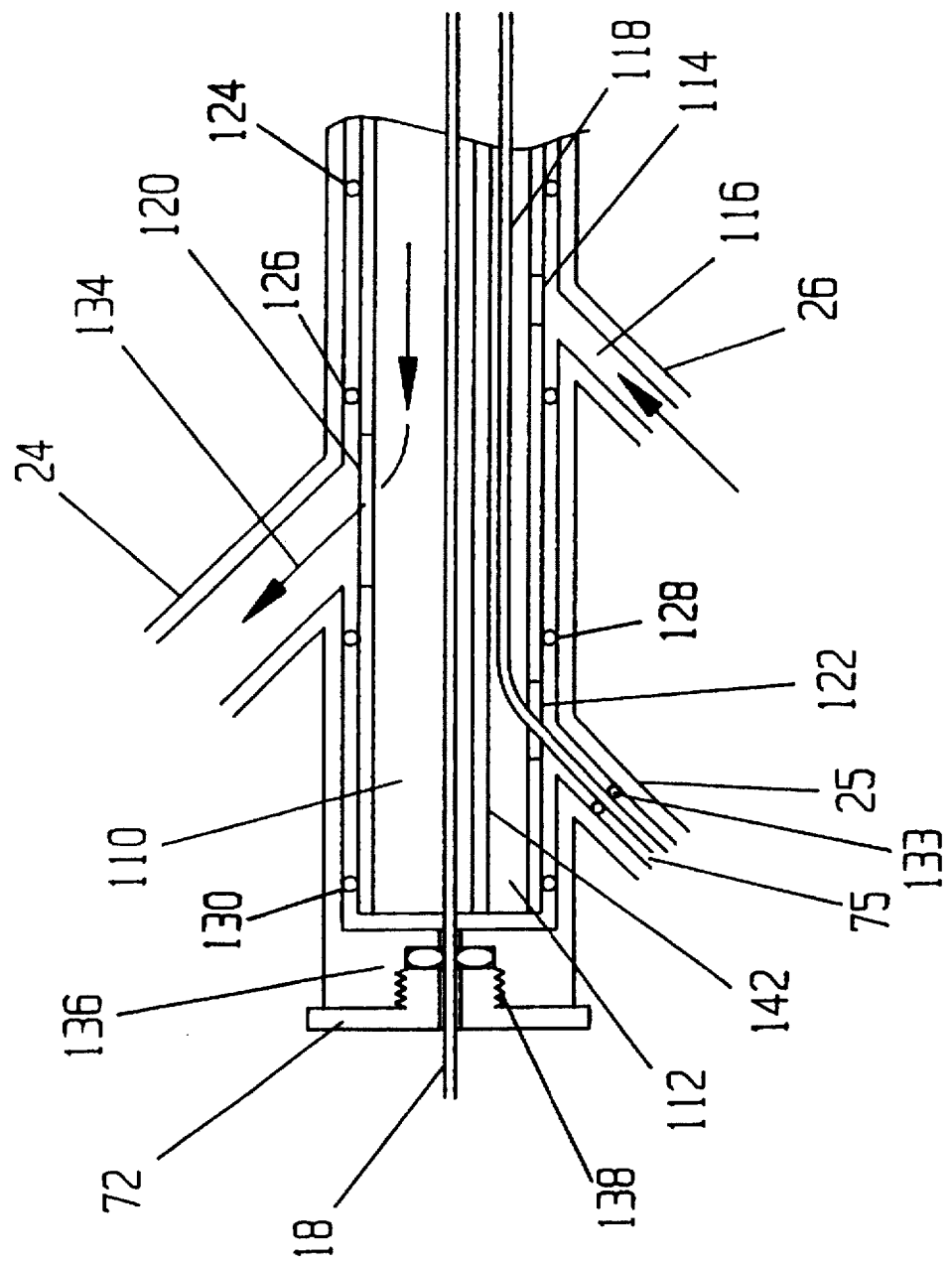
FIG. 4 is a conceptual view of the operation of the manifold.

FIG. 4 is a schematic view of manifold 20 wherein all referenced elements are as previously described. This figure is purposely not drawn to scale to better illustrate the operation of manifold 20.

Figure 5A:
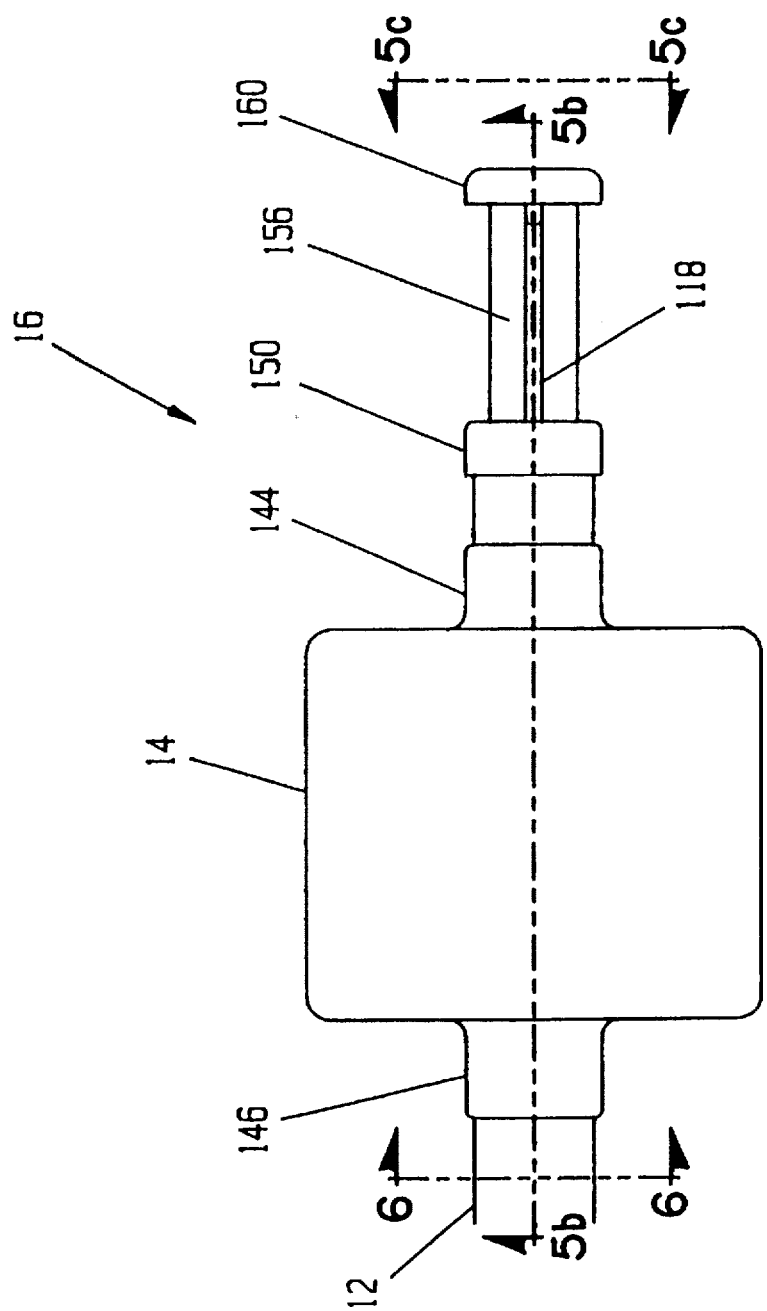
FIG. 5a is a close up view of the distal end of the catheter system of the present invention.

FIG. 5a is a close up view of balloon 14 and distal tip 16 of catheter 12. Attachment between catheter 12 and balloon 14 occurs at overlap points 144 and 146. These overlap points are sealingly attached with adhesive or heat sealing.

Catheter 12 is a dual lumen catheter extruded from rubber or a polymer as described above. Cap 150 is fixedly attached at the distal tip of catheter 12 as shown. Preferably cap 150 is made of a radiopaque metal such as platinum, tantalum or stainless steel to provide ease of location under fluoroscopy.

Extending beyond cap 150 is metallic tubing 118. This is necessary to permit the jet or jets which dispense the saline solution to be directed at cap 150 (i.e. the distal tip of lumen 110). Because metallic tubing 118 is so flexible, it must be backed by metal plate 156 to provide the necessary rigidity. Metallic tubing 118 is bent as explained below. To conform, metal plate 156 is angled to form rounded distal surface 160. This annular shaped tip would allow passage of a guide wire, angioscope, or angioplasty dilatation catheter.

Figure 5B:
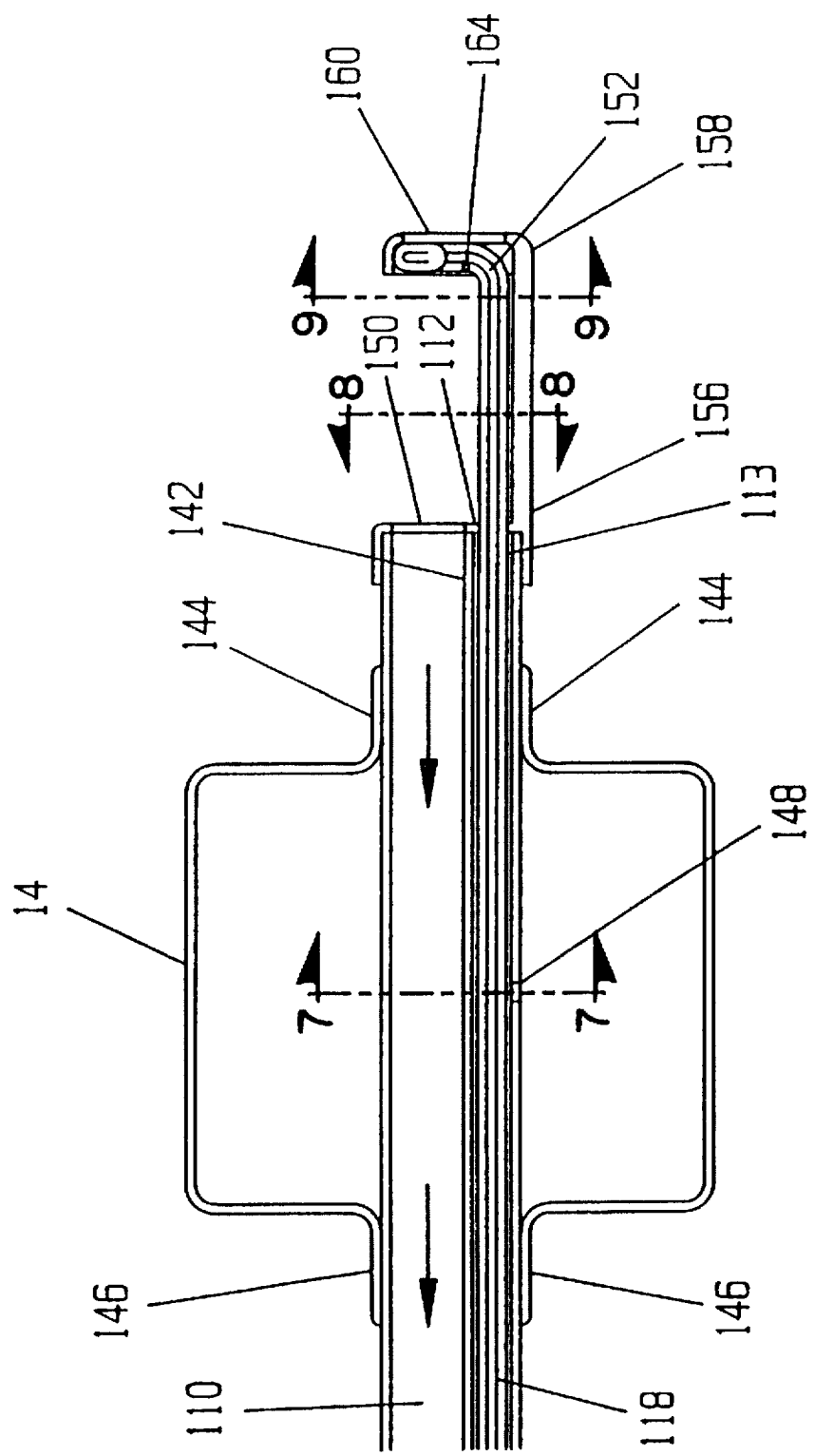
FIG. 5b is a longitudinal sectioned view of the distal end of the catheter system.

FIG. 5b is a longitudinal sectioned view of the structure of FIG. 5a, wherein referenced elements are as previously described. Also shown in this view is balloon inflation port 148 which provides fluid communication between lumen 112 and balloon 14. Septum 142 separates lumen 110 from lumen 112. Lumen 112 is sealed distal to the balloon using an adhesive seal 113 attaching the high pressure tube 118 and filling lumen 112.

Metallic tubing 118 is bent into a circular shape perpendicular to the axis of the catheter beginning at bend 152. Metal plate 156 bends at point 158 to provide rigidity at that point. Jet 164 is a small diameter orifice on the order of 0.0005 to 0.003 of an inch. It directs a stream of saline solution at cap 150 (i.e. mouth of lumen 110) at 5,000 to 30,000 psi. This pressure is sufficient to emulsify thrombus deposits located between jet 164 and cap 150. This stream of saline solution also creates a stagnation pressure about cap 150 sufficient to propel the emulsion into and through lumen 110 (see also FIG. 1). This stream of saline solution is of high velocity which creates a localized area of low pressure around the stream which attracts thrombus deposits for emulsification and removal.

Figure 5C:
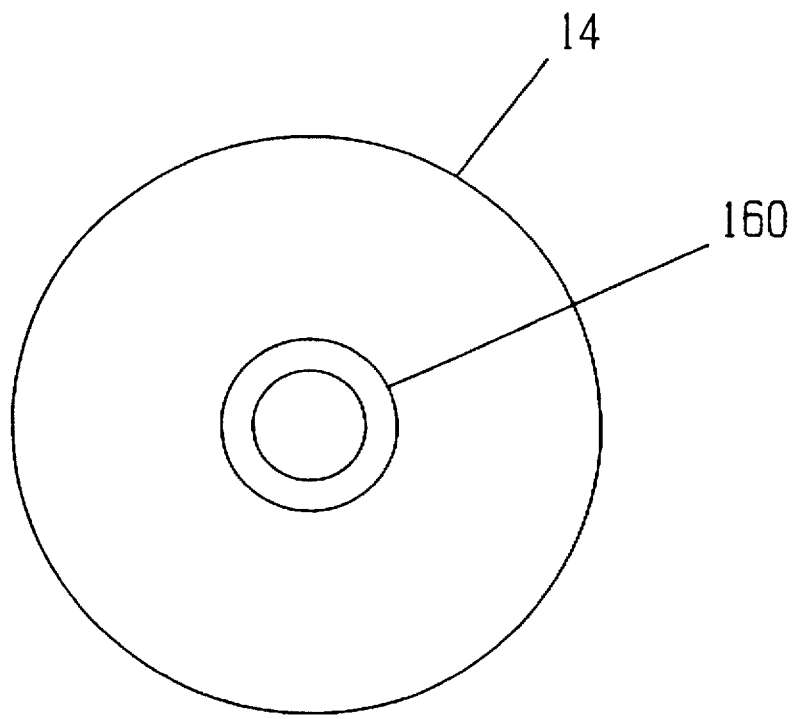
FIG. 5c is a view from the distal end of the catheter system.

FIG. 5c is a view from the distal end of catheter system 10 wherein referenced elements are as described above. The central opening would allow passage of a guide wire, angioscope or angioplasty dilatation catheter.

Figure 6:
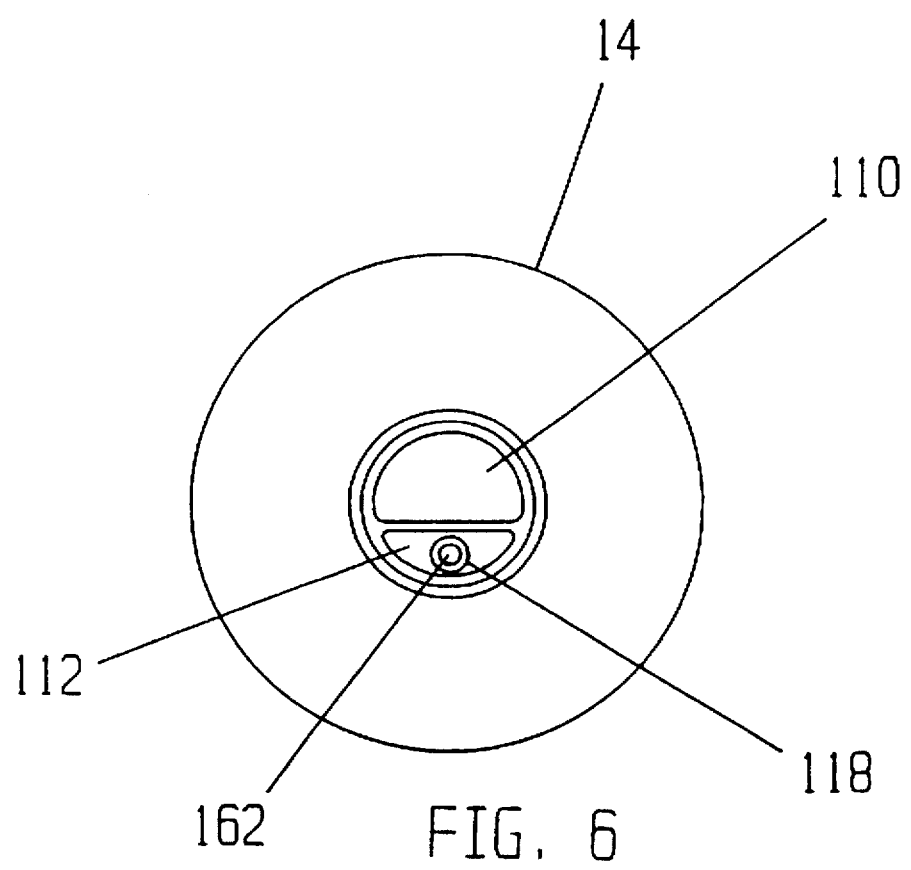
FIG. 6 is a cross-sectional view from immediately proximal of the balloon.

FIG. 6 is a cross-sectional view from the proximal end of catheter 12 to balloon 14, wherein referenced elements are as previously described. Metallic tubing 118 is shown within lumen 112. The cross-sectional area of lumen 112 which is in excess of that needed for metallic tubing 118 provides the fluid passageway for inflation of balloon 14. Lumen 162 of metallic tubing 118 has a diameter of about 0.003–0.010 inch. It conveys saline solution at 1,000 to 30,000 psi through the main body of the catheter.

Figure 7:
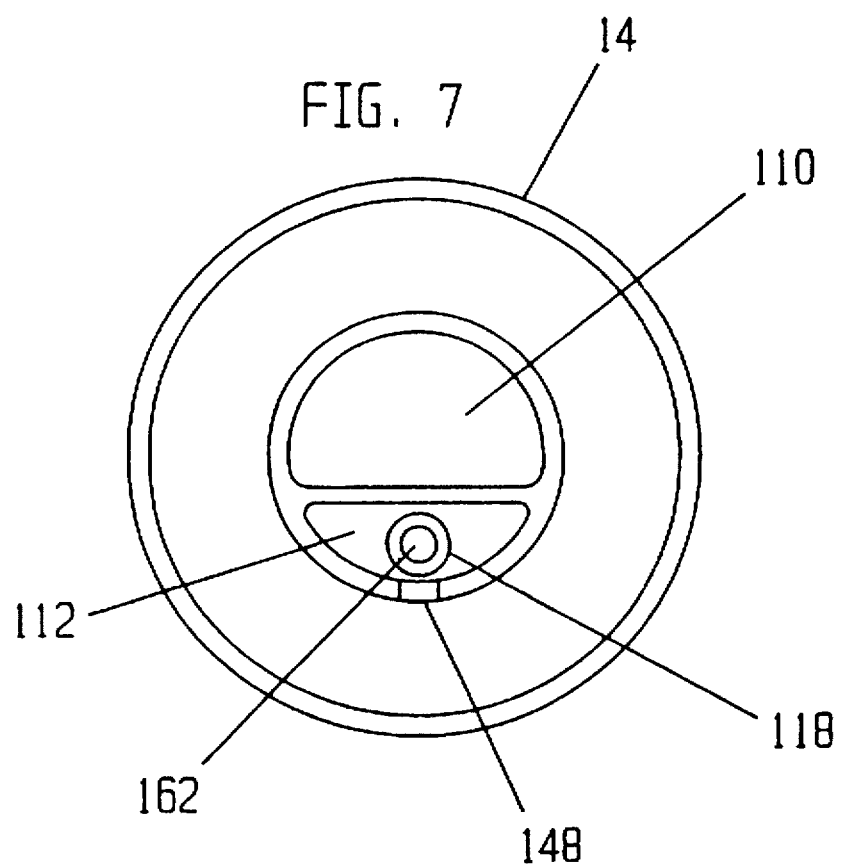
FIG. 7 is a cross-sectional view across the balloon inflation port.

FIG. 7 is a cross-sectional view taken through balloon 14 and balloon inflation port 148. The remaining elements are as previously described.

Figure 8:
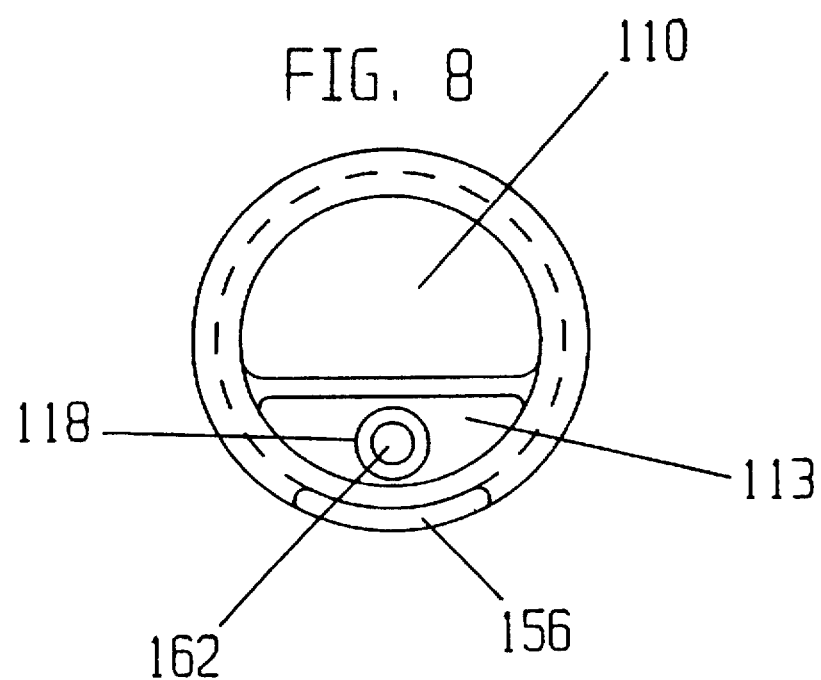
FIG. 8 is a cross-sectional view taken distal of the balloon.

FIG. 8 is a cross-sectional view taken distal to balloon 14. The distal end of the balloon inflation lumen is plugged with adhesive 113 to provide an enclosed space for balloon inflation.

Figure 9:
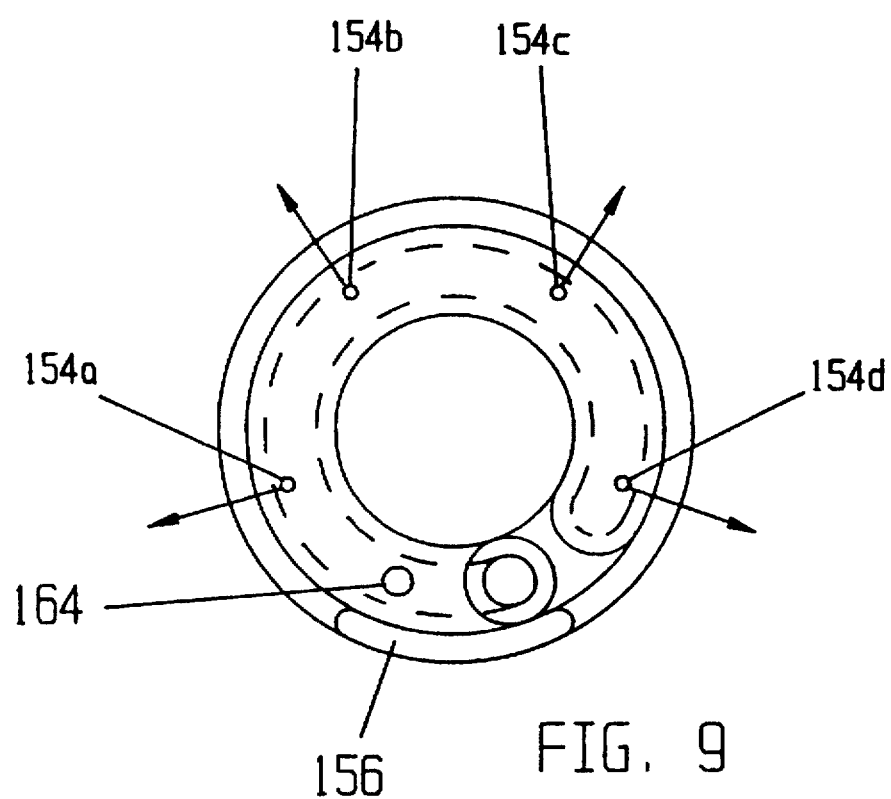
FIG. 9 is a cross-sectional view taken near the distal tip of the catheter system.

FIG. 9 is a cross-sectional view taken just proximal of the saline solution jets. Shown in addition to jet 164 are jets 154a, 154b, 154c, and 154d, which are similar in size and range to jet 164. Jet 164 is directed generally back toward the evacuation channel to generate a stagnation pressure, create a localized area of low pressure to attract thrombus deposits, emulsify any thrombus which is brought into its path and keep the opening to the evacuation lumen clean and open.

Jets 154a, 154b, 154c, and 154d can number from zero to eight with a preferred number of three to six jets, although not limiting and are directed with some radial component toward the vessel wall as drawn and may also have some axial direction towards the evacuation opening. These jets remove thrombus which is attached to the vessel wall and establish a recirculation pattern which entrains thrombotic material and brings it into contact with jet 164 for further emulsification and removal.

Figure 10:
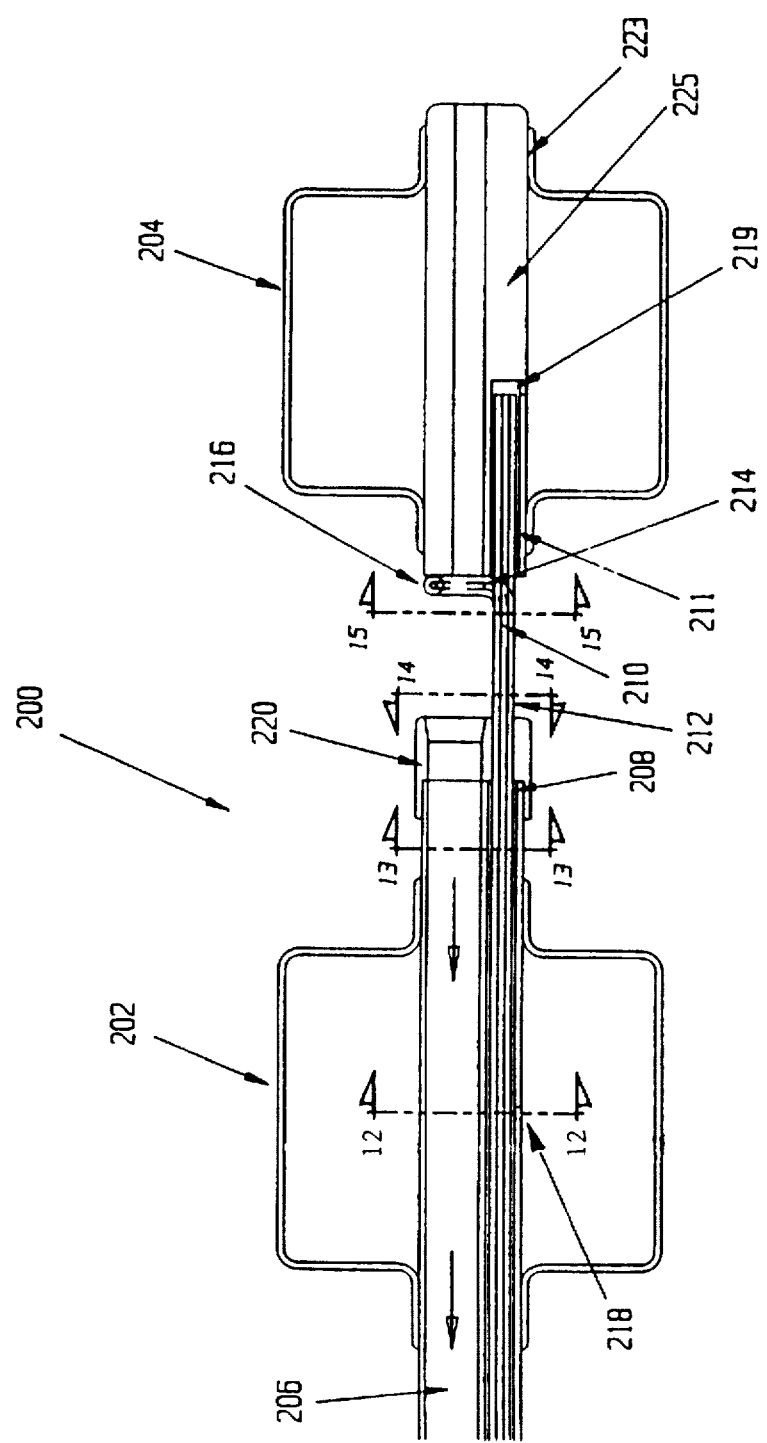
FIG. 10 is a longitudinal sectioned view of the distal end of a catheter system employing an alternative embodiment of the present invention.

FIG. 10 is a close up view of the distal end of an alternative embodiment of the present invention including balloon 204 which is located distal to the active components. Balloon 204, along with balloon 202, can be used to isolate a portion of the vessel during the procedure. Fluid recirculation between the balloons brings the thrombus into contact with the jet for emulsification and removal. In this embodiment, lumens 206 and 208 function as lumens 110 and 112, respectively. Cap 220 is similar to cap 150. A thermistor (not shown) can be used with either the preferred or alternative embodiment. The thermistor concept should only be added as a possibility which will help in monitoring the degree of occlusion and/or power delivery. Metal tube 212 has the same function as metal plate 156 in the preferred embodiment. Metallic tubing 210, bend 214 and jet 216 directly correspond to similar components in the preferred embodiment. An adhesive 221 and 223 is applied in the lumen of distal tubing 225 to provide an enclosed space and allow balloon 204 to be inflated through the distal balloon inflation port 219.

Figure 11:
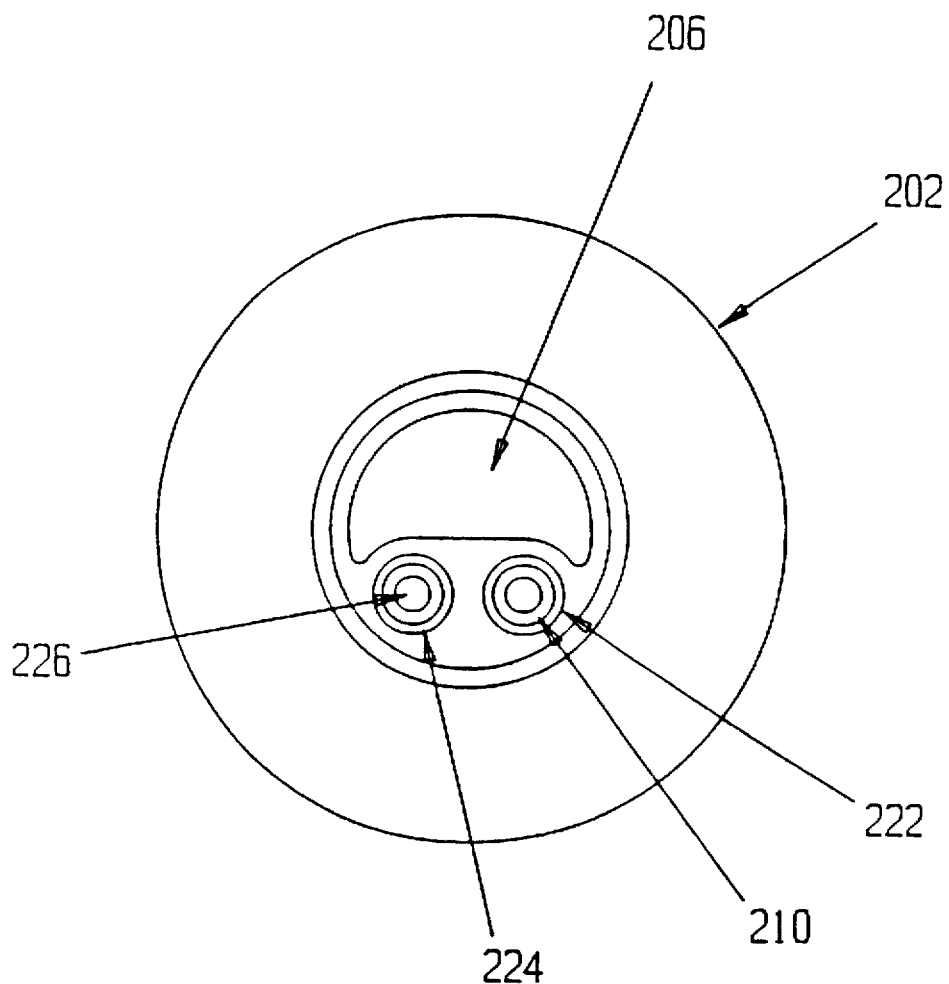
FIG. 11 is a cross-sectional view taken proximal to the proximal balloon of the alternative embodiment.

FIG. 11 is a cross-sectional view of the alternative embodiment from proximal to balloon 202. In this embodiment, a three lumen catheter is used. Lumen 206 is the largest lumen, which is used for passage of the guide wire and evacuation of the effluent. Annular space 222 is used for inflation of balloon 202 and for passage of metallic tubing 210. Lumen 226 provides for inflation of balloon 204. Annular space 224 could be used to permit an external device (not shown) to measure the pressure and/or temperature within the treatment area to determine when thrombus deposits are completely emulsified.

Figure 12:
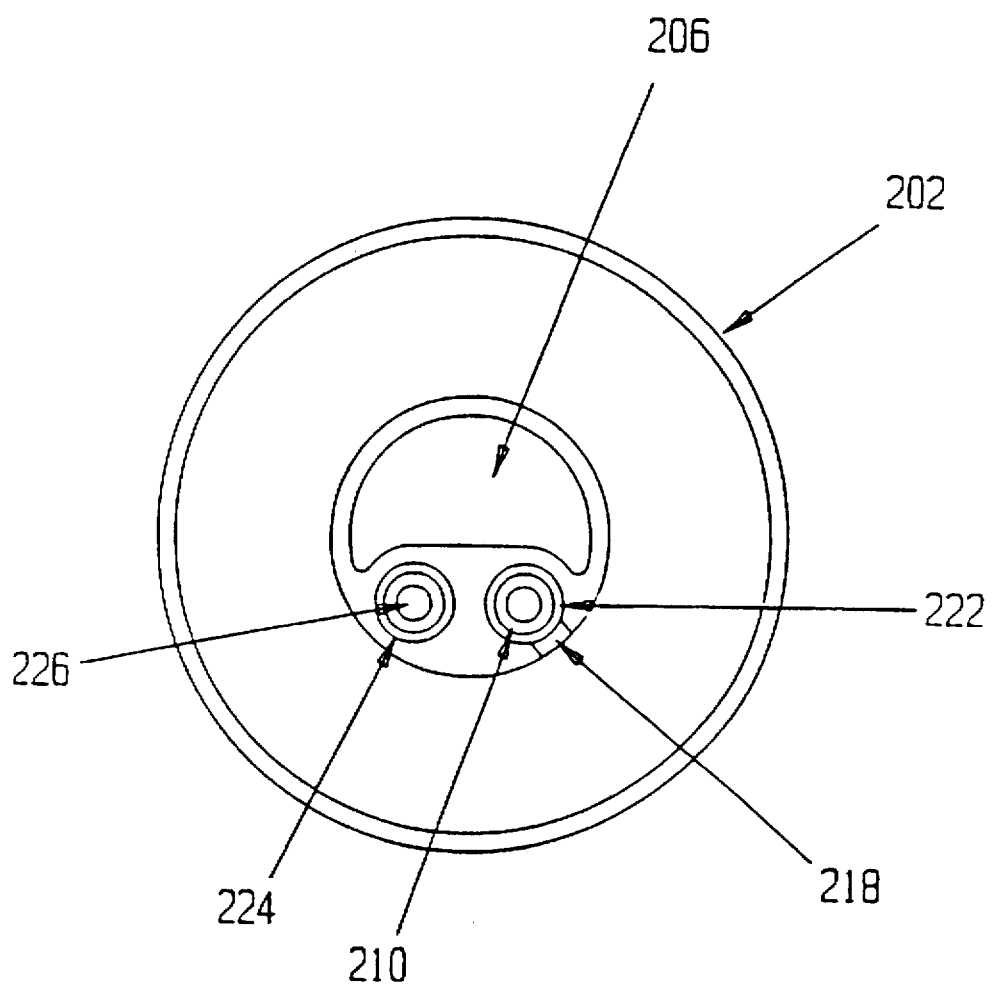
FIG. 12 is a cross-sectional view of the alternative embodiment from the inflation port of the proximal balloon.

FIG. 12 is a cross-sectional view of the alternative embodiment as viewed through balloon 202. Shown is balloon inflation port 218.

Figure 13:
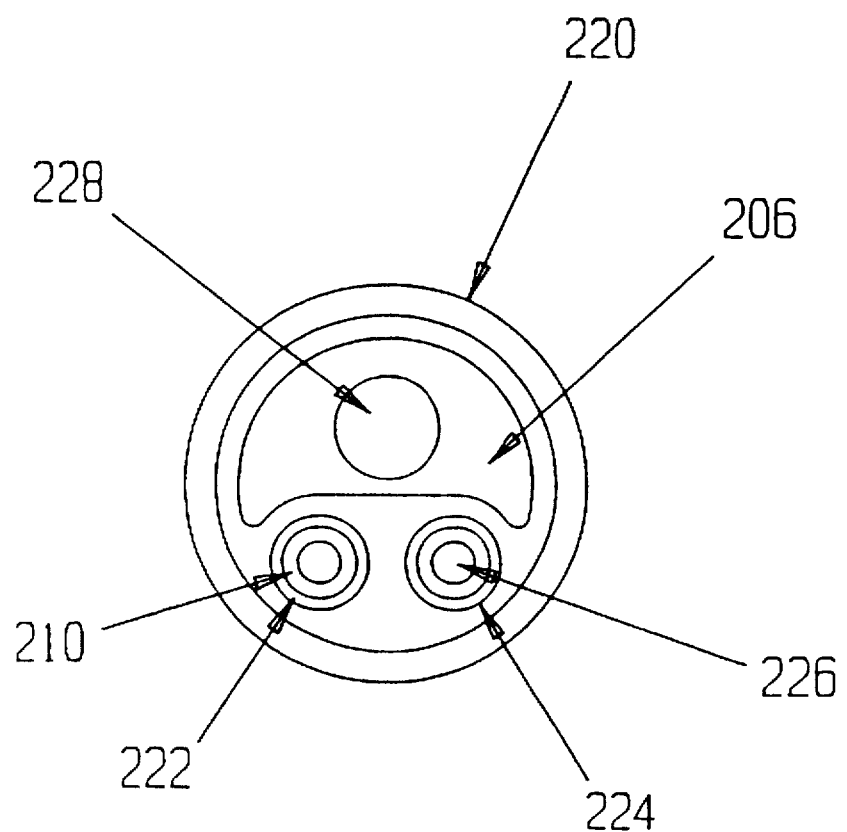
FIG. 13 is a cross-sectional view of the alternative embodiment taken distal of the proximal balloon.

FIG. 13 is a cross-sectional view of the alternative embodiment as viewed distal of balloon 202. Guide wire 228 is shown located within lumen 206.

Figure 14:
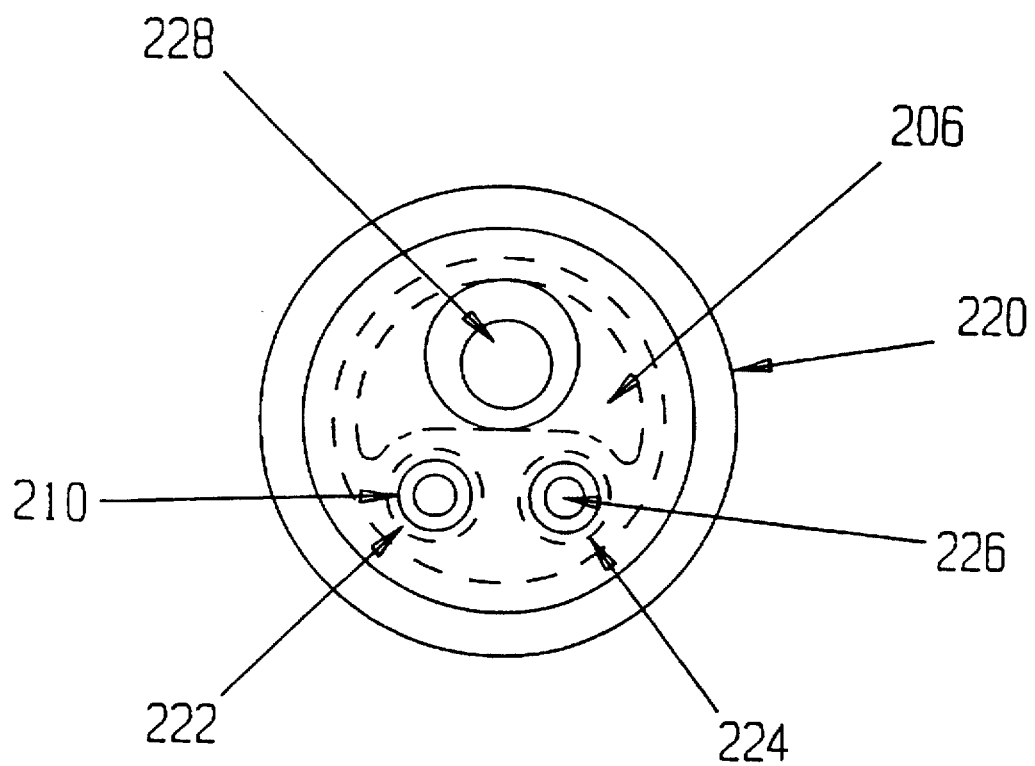
FIG. 14 is a cross-sectional view of the alternative embodiment taken distal of the mouth of the evacuation lumen.

FIG. 14 is a cross-sectional view of the alternative embodiment as viewed distal to cap 220.

Figure 15:
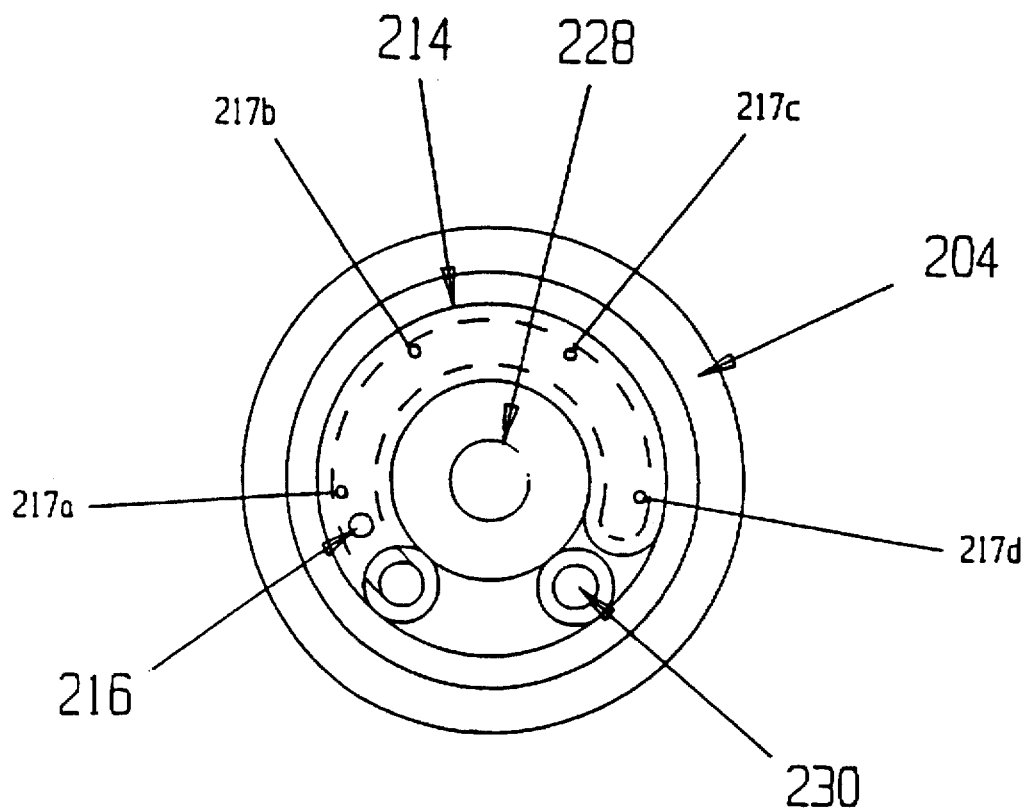
FIG. 15 is a cross-sectional view of the alternative embodiment taken proximal of the distal balloon.

FIG. 15 is a cross-sectional view of the alternative embodiment as viewed proximal to balloon 204. Shown is a jet 216 directed back towards the evacuation lumen and a plurality of jets numbered 217a, 217b, 217c and 217d, which are directed with some radial component toward the vessel wall. These outwardly directed jets may not be necessary since the distal balloon can be used to dislodge the thrombus off of the wall. Metal tubing 230 extends to the distal balloon for inflation.

FIG. 16a is a longitudinal sectioned view of safety monitor 44. It is placed over flexible membrane of distal end 42 and flexible effluent tubing 54. Fluid communication is supplied by port 332.

FIG. 16b is a cross sectioned view of safety monitor 44. It functions much as a safety monitor with contacts 336 and 340 being closed whenever pressures are reduced due to blockage of the evacuation tube. Fluid communication to the membrane is supplied by port 332.

Various modifications can be made to the present invention without departing from the scope thereof.

We claim:

1. A device for removing thrombus or other tissue from an occluded or obstructed biological or synthetic body vessel comprising:

a. a tubular member having a proximal end and a distal end, having a first passage and a second passage and a third passage extended along the length thereof, each passage with a proximal and distal end;

b. said first passage comprising tubular means which comprises one or more orifices forming one or more liquid jets emanating from said distal end of said first passage;

c. said second passage comprising tubular means for carrying a flow of fluid and emulsified tissue from said distal end to said proximal end, said distal end of said second passage being open;

d. said one or more liquid jets emanating from said distal end of said first passage impinges on said open distal end of said second passage with a component in the direction of the flow of fluid and emulsified tissue in said second passage, said liquid jet(s) providing sufficient stagnation pressure without any suction means required to drive the flow of fluid and emulsified tissue from said distal end of said second passage towards said proximal end of said second passage;

e. said proximal end of said first passage is connected to a high pressure liquid source, said high pressure liquid source provides a flow of high pressure liquid to said proximal end of said first passage;

f. said proximal end of said second passage provides removal of the flow of fluid and emulsified tissue said proximal end of said second passage being open; and, g. said third passage comprising tubular means for providing communication between said proximal and distal ends of said tubular member.

2. A device for removing thrombus or other tissue from an occluded or obstructed biological or synthetic body vessel comprising:

a. a tubular member having a proximal end and a distal end, having a first passage and a second passage and a third passage extended along the length thereof, each passage with a proximal and distal end;

b. said first passage comprising tubular means which comprises one or more orifices forming one or more liquid jets emanating from said distal end of said first passage;

c. said second passage comprising tubular means for carrying a flow of fluid and emulsified tissue from said distal end to said proximal end, said distal end of said second passage being open;

d. said one or more liquid jets emanating from said distal end of said first passage to produce a low pressure region which tends to bring the thrombus or other tissue towards said jet(s) thereby avoiding the need to move said jet(s) into immediate juxtaposition with the thrombus or other tissue or aiming said jets directly at the thrombus or other tissue;

e. said proximal end of said first passage is connected to a high pressure liquid source, said high pressure liquid source provides a flow of high pressure liquid to said proximal end of said first passage;

f. said proximal end of said second passage provides removal of the flow of fluid and emulsified tissue, said proximal end of said second passage being open; and, g. said third passage comprising tubular means for providing communication between said proximal and distal ends of said tubular member.

3. A device for removing thrombus or other tissue from an occluded or obstructed biological or synthetic body vessel comprising:

a. a tubular member having a proximal end and a distal end, having a first passage and a second passage and a third passage extended along the length thereof, each passage with a proximal and distal end;

b. said first passage comprising tubular means which comprises one or more orifices forming one or more liquid jets emanating from said distal end of said first passage;

c. said second passage comprising tubular means for carrying a flow of fluid and emulsified tissue from said distal end to said proximal end, said distal end of said second passage being open;

d. said proximal end of said first passage is connected to a high pressure liquid source, said source providing a flow of high pressure liquid at pressure sufficient to supply said proximal end of said first passage with a high pressure liquid at greater than approximately 1000 psi, allowing for pressure losses along said first passage, resulting in decreased pressure at said distal end of said first passage;

e. said one or more liquid jets emanating from said distal end of said first passage impinges on said open distal end of said second passage with a component in the direction of the flow of fluid and emulsified tissue in said second passage;

f. said proximal end of said second passage provides removal of the flow of fluid and emulsified tissue, said proximal end of said second passage being open; and, g. said third passage comprising tubular means for providing communication between said proximal and distal ends of said tubular member.

4. The device of claim 1, 2 or 3 wherein a balloon isolation means is attached to said tubular member at a point proximal to said liquid jets, said isolation means communicating with said distal end of said first passage, said isolation means thereby being actuated from said proximal end of said tubular member by communication with said first passage.

5. The device of claim 1, 2 or 3 wherein a balloon isolation means is attached to said tubular member at a point distal to said liquid jets, said isolation means communicating with said distal end of said third passage, said isolation means thereby being actuated from said proximal end of said tubular member by communication with said third passage.

6. The device of claim 1, 2 or 3 wherein a balloon isolation means is attached to said tubular member at points proximal to said liquid jets and distal to said liquid jets, said isolation means attached proximal to said liquid jet(s) communicating with said distal end of said first passage, and said isolation means distal to said liquid jet(s) communicating with said distal end of said third passage.

7. The device of claim 6 wherein said isolation means serves to enhance fluid recirculation in the vicinity of said liquid jets.

8. The device of claim 1, 2 or 3 wherein a balloon dilation means is attached to said tubular member, providing for dilation of the biological or synthetic body vessel, said dilation means communicating with said distal end of said first passage, said dilation means thereby being actuated from said proximal end of said tubular member by communication with said first passage.

9. The device of claim 8 wherein a metering means is connected to said proximal end of said second passage to control the flow of fluid and emulsified tissue in said second passage at a rate of flow less than the rate of flow which would result without said metering means.

10. The device of claim 1, 2 or 3 wherein said first passage comprises a metal tube.

11. The device of claim 1, 2 or 3 wherein said first passage comprises a tube constructed of a high-strength polymer material.

12. The device of claim 1, 2 or 3 wherein a metering means is connected to said proximal end of said second passage to control the flow of fluid and emulsified tissue in said second passage at a rate of flow that is less than the rate of flow which would result without said metering means.

13. The device of claim 12 wherein said metering means consists of a roller pump which controls the flow of fluid and emulsified tissue in said second passage.

14. The device of claim 12 wherein said metering means controls the flow of fluid and emulsified tissue in said second passage at a rate of flow approximately equal the rate of the flow of high pressure liquid in said first passage.

15. The device of claim 1, 2 or 3 wherein one or more liquid jets emanating from said distal end of said first passage are directed with some radial component.

16. The device of claim 1, 2 or 3 wherein said high pressure liquid source is a positive-displacement piston pump.

17. The device of claim 16 wherein said piston pump provides the flow of high pressure liquid in a largely pulsatile or periodic unsteady flow.

18. The device of claim 16 wherein said piston pump provides the flow of high pressure liquid in a largely steady flow.

19. The device of claim 1, 2 or 3 wherein said second passage also provides passage for a guidewire device.

20. The device of claim 1, 2 or 3 wherein said third passage provides passage for liquid medium, and provides communication between said proximal and distal ends of said tubular member.

21. The device of claim 1, 2 or 3 wherein said distal end of said first passage is formed into an arcuate shape extending beyond said second passage to direct at least one jet(s) onto said distal end of said second passage.

22. The device of claim 1, 2 or 3 wherein said distal end of said first passage is formed into a toroidal shape which is oriented in a plane perpendicular to a longitudinal axis of said tubular member.

23. The device of claim 22 wherein a plurality of liquid jets emanate from various points along said toroidal-shaped portion of said first passage; when a guidewire device is in position through said toroidal shape, said liquid jets are therefore oriented at various points circumferentially around the guidewire device, thereby decreasing any effect that the guidewire device may have in shielding any tissue from the effects of said jets.

* * * * *